(12) United States Patent
de Vandiere et al.

(10) Patent No.: US 9,494,514 B2
(45) Date of Patent: Nov. 15, 2016

(54) METHODS AND SYSTEMS FOR ANALYZING AIRBORNE COMPOUNDS

(71) Applicant: Societe Flowgene, Saint Beauzire (FR)

(72) Inventors: Bruno de Vandiere, Saint Beauzire (FR); Claude Debroche, Cebazat (FR); Nicolas Garnier, Sainte Croix en Jarez (FR)

(73) Assignee: Flowgene, Saint Beauzire (FR)

( * ) Notice: Subject to any disclaimer, the term of this patent is extended or adjusted under 35 U.S.C. 154(b) by 366 days.

(21) Appl. No.: 13/871,771

(22) Filed: Apr. 26, 2013

(65) Prior Publication Data

US 2013/0234046 A1 Sep. 12, 2013

Related U.S. Application Data

(63) Continuation of application No. PCT/FR2011/000574, filed on Oct. 25, 2011.

(30) Foreign Application Priority Data

Nov. 2, 2010 (FR) ...................................... 10 04323

(51) Int. Cl.
| | | |
|---|---|---|
| F21V 9/16 | (2006.01) | |
| G01N 21/64 | (2006.01) | |
| G01N 33/00 | (2006.01) | |
| G01N 27/447 | (2006.01) | |

(52) U.S. Cl.
CPC ............ *G01N 21/64* (2013.01); *G01N 27/447* (2013.01); *G01N 33/00* (2013.01); *G01N 21/6486* (2013.01)

(58) Field of Classification Search
CPC ............................. G01N 33/00; G01N 27/447
See application file for complete search history.

(56) References Cited

U.S. PATENT DOCUMENTS

| | | | |
|---|---|---|---|
| 3,946,239 A | 3/1976 | Salzman et al. | |
| 2003/0015019 A1* | 1/2003 | O'Brien | ......................... 73/23.2 |
| 2004/0232052 A1* | 11/2004 | Call et al. | ..................... 209/143 |
| 2007/0085023 A1 | 4/2007 | Debroche | |
| 2008/0183094 A1 | 7/2008 | Schonfuss et al. | |

FOREIGN PATENT DOCUMENTS

| | | |
|---|---|---|
| EP | 0361068 A2 | 4/1990 |
| FR | 2890747 A1 | 3/2007 |
| WO | 9531721 A1 | 11/1995 |

OTHER PUBLICATIONS

"224 nm deep-UV laser for native fluorescence, a new opportunity for biomolecules detection", Journal of Chromatography A, 1156 (2007) 94-100 to Bonnin et al.*

(Continued)

*Primary Examiner* — David J Makiya
*Assistant Examiner* — Kenneth J Malkowski
(74) *Attorney, Agent, or Firm* — Kenneth H. Ohriner; Perkins Coie LLP (57) ABSTRACT

In systems and methods for analyzing traces of airborne compounds, the air to be analyzed is circulated for a given length of time through a small-diameter analysis tube while lowering the temperature of the air at the entrance to the analysis tube. Condensation and deposits of compounds are formed on the inner walls of the analysis tube. A scraping liquid is circulated through the analysis tube to scrape off the deposits. The compounds in the deposits are concentrated at the front of this liquid. The front of the liquid is then analyzed to identify the compounds.

18 Claims, 5 Drawing Sheets

(56) References Cited

OTHER PUBLICATIONS

Paquette, D.M. et al: "Capillary Electrophoresis with laser-induced native fluorescence detection for profiling body fluids", Journal of Chromatography B: Biomedical Sciences & Applications, Elsevier, Amsterdam, NL, vol. 714, No. 1, 28 août 1998 (Aug. 28, 1998), pp. 47-57.

Office Européen Des Brevets, International Search Report dated Dec. 16, 2011 in PCT/FR2011/000574.

* cited by examiner

Fig 12

METHODS AND SYSTEMS FOR ANALYZING AIRBORNE COMPOUNDS

PRIORITY CLAIMS

This application is a continuation of International Patent Application No. PCT/FR2011/000574 filed Oct. 25, 2011 and now pending which claims priority to French Patent Application No. 10 04323 filed Nov. 2, 2010, both incorporated herein by reference.

TECHNICAL FIELD

Smell detection has always been a major research area and represents a particularly ambitious challenge: the goal is nothing less than replacing the olfactory organ commonly known as a "nose" in higher mammals with an instrument.

The first significant work on this subject appeared in the early fifties. Much later, in 1982, the first "electronic nose" appeared (K. Persaud, G. Dodd, Nature 1982, 299, 352-355). The device developed by Persaud and Dodd uses a network of chemical sensors which change conductivity when exposed to a smell or a vapor. Analyzing the response of these sensors offers the possibility of giving a signature to a smell and therefore recognizing it. This principle was later taken up again by other research groups, and new families of sensors appeared. The most commonly used sensors are electronic. However, these electronic sensors are extremely sensitive to humidity and temperature. They work only in a highly specific environment which limits their use to very precisely defined fields of application. Newer smell-detection techniques relying on advanced analytical chemistry use ultra-fast gas chromatography combined with mass spectrometry.

In the area of the biological functioning of the nose, in 1991, Richard Axel and Linda Luck demonstrated the existence of olfactory receptors in the sense organs of higher mammals. They studied the functioning of olfactory receptors in order to extract specific receptors capable of sensing a smell or, more precisely, an odorous molecule. This work showed the special role of certain proteins which change shape after capturing an odorous molecule. A device using the Raman Effect, as described in French Patent No. FR 2,890,747, was developed to identify the change in shape of these proteins. However, so-called biological sensors are exceedingly delicate to implement and currently have not developed beyond the status of a laboratory experiment.

SUMMARY OF THE INVENTION

The present invention proposes an alternate and relatively simple method to capture, detect, identify and quantify the compounds contained in air. In the following description, "compounds" is intended to broadly mean particles or a set of particles in suspension in the air, including spores, odorous molecules and volatile organic compounds (VOCs).

In one aspect, the invention combines a procedure to obtain compound samples, a procedure for manipulating and sensing these compound samples, an optical procedure based on the emission of a fluorescence signal induced by a deep-UV laser (<300 nm) and a separation analysis procedure of the capillary electrophoresis type which enables identifying and quantifying the compounds.

The inventors have observed that aspiration of an air sample within an enclosure containing suspended compounds results in a deposit or a dirtying of the analytical tube. The deposit is most commonly located toward the analytical tube inlet. The deposit is made up of compounds contained in the air. The speed of formation of the deposit is related to the dimensions of the analysis tube (cross-section and length), to the material used to make the analysis tube, to the air flow rate used to physically obtain the sample, and to thermal conditions surrounding the analysis tube. When a liquid is introduced to clean the inner surface of the analysis tube, the compounds are concentrated mainly at the front of the liquid.

Correspondingly, a method of the invention may be based on an analysis of the traces of compounds present in a volume of air by circulating air through a small-diameter analysis tube while lowering the temperature of the air at the entrance to the analysis tube. The humidity or water vapor in the air condenses on the inner walls of the analysis tube and triggers the deposit of compounds on the tube walls. A scraping liquid is circulated through the analysis tube liquid and scrapes off the deposited compounds in such a way that the compound traces are concentrated at the front of the scraing liquid. The presence, nature or concentration of the compounds picked up on this front are then determined.

In this way, compounds present in the air of the unit to be analyzed are trapped on the inner surface of the capillary tube by the condensation of humidity contained in the air.

Since these compounds are preferentially concentrated in the front of the scraping liquid, they can then be analyzed using appropriate and well-known detection methods. This provides a simple and relatively inexpensive way to analyze the air and the compounds it contains, such as VOCs or other compounds ordinarily detectable by smell.

The analysis tube may be a capillary type tube having an internal diameter of less than 700 µm. In a first procedure, the temperature is lowered by creating a low pressure zone at the outlet end of the capillary analysis tube, to cause an adiabatic expansion of the air entering the capillary tube. The air may optionally be cooled at the analysis tube inlet using refrigeration around the exterior wall of the analysis tube, with or without also using adiabatic expansion. The spectral response is analyzed when the front of the scraping liquid passes by a detector cell which determines the presence of compound traces on the front, optionally using a native fluorescence detection method.

The air contained in the volume of air can be analyzed in a meaningful way at given time intervals to define the evolution over time of spectral responses triggered by compound traces. It may also be useful to collect the front of the scraping liquid containing the compounds in a container located at the analysis tube outlet end. At the end of the process, the composition and concentration of components present in the front may also optionally be determined using capillary electrophoresis.

The same capillary tube may also be used to collect compound traces and carry out a native florescence analysis and a capillary electrophoresis analysis of the compounds contained in the front of the scraping liquid.

A system for analyzing compound traces present in the air may include a fluorescence detector having a deep-UV laser which emits an excitation beam on a flow of matter circulating in an analysis tube made of a transparent material, an optical device which enables targeting this excitation, and a light detector to collect the fluorescence emitted by the flow of matter. Circulation methods may enable the successive transmission of a liquid flow and a gaseous flow inside the analysis tube from the inlet to the outlet ends. The system may include refrigeration for cooling the analysis tube inlet. Circulation may be provided by an aspiration pump which is able to create vacuum at the outlet end of the analysis tube and which has a flow rate adjusted to create an adiabatic expansion at the analysis tube inlet to cool the air entering the analysis tube.

The system may include a way to direct the analysis tube inlet end toward the volume of air to be analyzed, toward a bottle containing a scraping liquid, toward a bottle containing a buffer liquid or toward a receptacle in which a volume of liquid containing the compounds to be analyzed can be collected. The analysis tube may be a capillary tube with a diameter under 700 μm.

The system may include an elliptical cavity of revolution arranged in such a way that the beam and the analysis tube pass in front of the optical device through passageways fitted inside the optical device. The axis of the laser beam and the axis of the analysis tube may be centered on one of the focal points of the optical device and are orthogonal to the axis of revolution of the optical device, creating an angle of less than 90° between them. In this way that the point of excitation of the flow of matter circulating inside the analysis tube corresponds to the focal point of the cavity. Light from the flow of matter circulating inside the analysis tube and emitted or transmitted through a properly located opening near the second focal point of the optical cavity can be collected from outside the device.

The methods and systems described may be used for the detection and identification of compounds in suspension within a closed or open atmosphere.

BRIEF DESCRIPTION OF THE DRAWINGS

The invention will be easier to understand and its advantages will become evident from reading the following description, which is given as a non-limitations example shown in FIGS. 1-12.

DETAILED DESCRIPTION OF THE DRAWINGS

A. Systems

Figure 1:
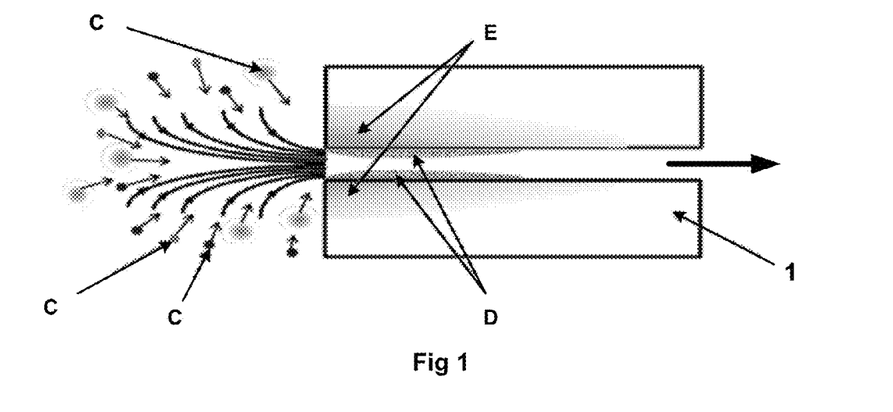
FIG. 1 is a schematic view of a compound deposit occurring at an analysis tube inlet.

Referring to FIG. 1, aspiring a large flow of air (in relation to the internal cross-section of the analysis tube) produces an adiabatic expansion at the analysis tube (1) inlet (E), which lowers the temperature at the inlet (E). In turn, this lower temperature causes the condensation of humidity contained in the air and resulting in the deposit (D) of the compounds (C) contained in the gaseous flow. In addition, the presence of water vapor (or humidity) in the gaseous flow accelerates the depositing process. Thus, the taking of a sample of compound particles (C) rests on the principle of cooling the air circulating at the analysis tube (1) inlet (E) to trigger the deposit (D) of compounds contained in a gaseous flow circulating in the analysis tube.

Figure 4:
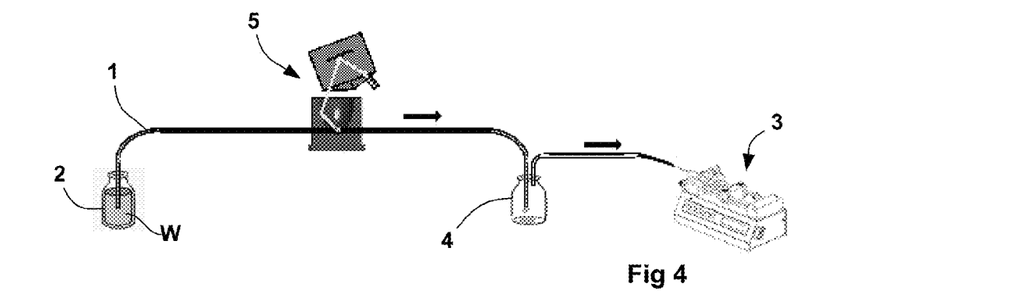
Figure 5:
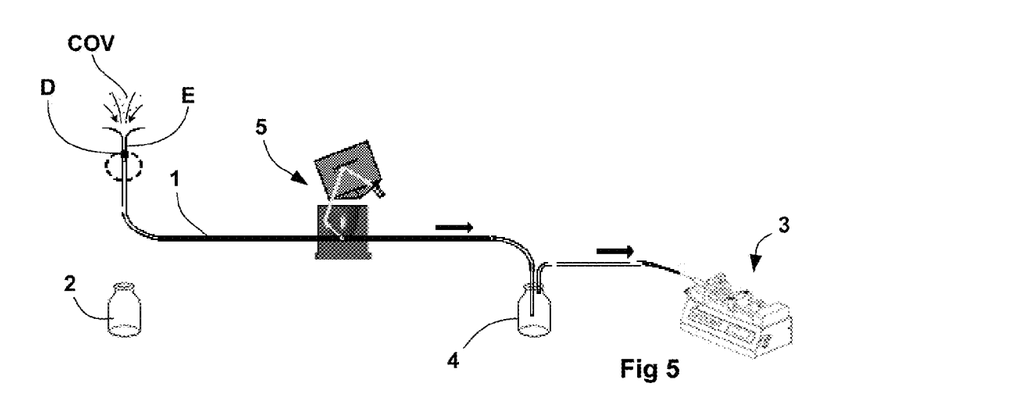

Turning to FIG. 5, an analysis tube (1) with one end forming the inlet (E) of the capillary tube may be placed inside an enclosure (2) containing air to be analyzed. Alternatively as shown in FIG. 3-4, 6 or 8, it may be put inside a bottle containing a gas or a liquid. If adiabatic expansion cooling is used, the result becomes more pronounced as tube diameter decreases and air flow increases.

Formation of a deposit is proportional to the inner surface area and air cooling is proportional to adiabatic expansion and thus to the volume aspired. The tube may therefore be selected to provide a large surface area relative to its volume. In this context, a capillary tube (1), such as a glass tube, may be used. Capillary tubes come in a wide variety of internal and external diameters and in varying lengths. They may also be provided with a protective covering which allows for handling without taking special precautions. In one example a glass capillary tube with a 375 μm external diameter is used. These tubes come with internal diameters (ID) ranging from 20 μm to 700 μm. A 75 μm-ID capillary tube works well for an electrophoresis separation.

Aspiration may be proved by a pump (3) placed at the outlet end of the analysis tube, creating a vacuum which generates a flow that can vary from 0.001 μl/h to 150 ml/min. The pump flow rate should be high enough to provide the largest possible adiabatic expansion at the inlet to the capillary tube. A syringe-type pump may be used.

Figure 3:
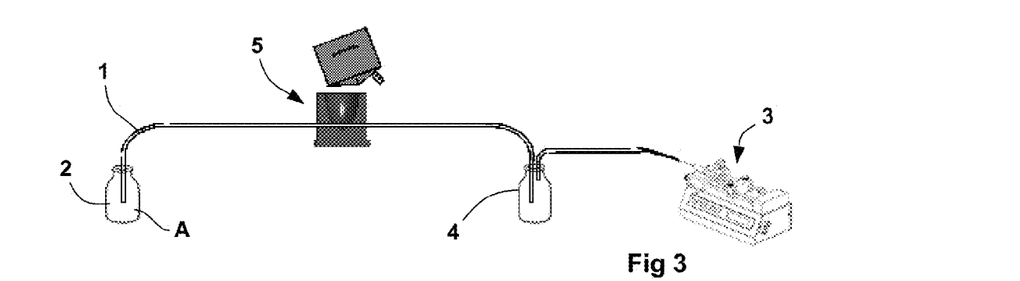
FIGS. 3 to 8 are schematic illustrations of the main steps of a detection method.

In FIG. 3, a sealed bottle (4) is installed between the second end of the capillary tube (1) and the pump (3). In this way, the pump (3) will create a vacuum in the sealed bottle, sucking up either liquids or gases which are introduced into the inlet end of the capillary tube.

To operate the system, the pump should be put on aspiration mode for a certain length of time to create the desired adiabatic expansion at the capillary tube inlet. The operating time necessary to ensure the deposit of a significant amount of particles is from one to ten minutes. As an alternative, air at the capillary tube inlet may be cooled using traditional methods such as placing a refrigeration coil around this inlet. A low-temperature liquid or gas circulates inside this tube. Another alternative is a Peltier-type apparatus. It is also possible to combine the effects of an adiabatic expansion with the effects produced by more traditional refrigeration methods. This might be necessary when the analysis tube diameter is too large for the aspiration methods used to create enough adiabatic expansion or when an accelerated formation of compound deposits is required.

Figure 2:
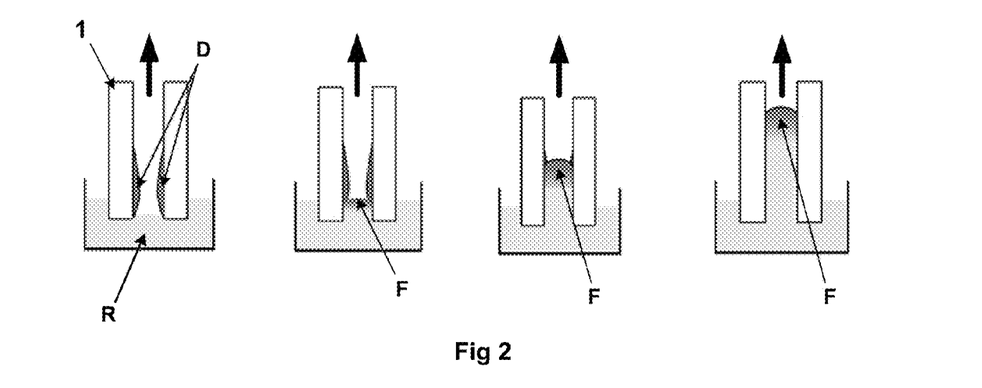
FIG. 2 is a schematic view in sequence of how a deposit on the front of the scraping liquid is captured.

With refrigeration, as the temperature drops, condensation occurring at the capillary tube inlet becomes more efficient and the time needed to obtain a useful amount of particles to be analyzed is shorter. As an example, when the temperature of the air sucked into the capillary tube inlet is lowered by an additional ten degrees Celsius, the time needed to form a deposit (D) is halved.

B. Collection of Deposits on the Internal Surface of the Analysis Tube

The liquid may be used to act as a piston. The traditional cleaning procedure used for an analysis tube involves circulating an appropriate liquid inside the tube. This liquid carries with it all the compounds (C) which cling to the inner wall of the analysis tube.

If the liquid viscosity is appropriate, the front of the liquid entering into the analysis tube (1) can act as a piston. As the liquid passes through the tube, the compounds (C) are scraped off the inner wall (this is the purpose of cleaning the tube). As illustrated in FIG. 2, it has been observed that these compounds (C) remain concentrated in the front (F) of the cleaning liquid without becoming dispersed throughout the liquid, which is designated in the following part of this presentation as the scraping liquid (R). Based on this observation the front (F) may be advantageously used to provide the test samples.

Under these conditions, it is therefore possible to analyze the presence of compounds (C) and, eventually, some of their characteristics when the front (F) passes by an appropriate detector. It is also possible to recover the front (F) of the scraping liquid (R), which contains the compounds (C) pulled off the walls of the analysis tube, to carry out subsequent analyses to identify the nature of these compounds.

As the analysis tube diameter increases, the viscosity of the scraping liquid (R) must also be increased to obtain the desired concentration of compounds (C) at the front of this liquid. On the contrary, viscosity will be much lower in a capillary tube. For a capillary tube with a 75 µm internal diameter, water, alcohol, sodium hydroxide and hydrochloric acid may be used without difficulty. For dimensions like these, the surface tension of the scraping liquid (R) takes precedence over the effects tied to viscosity. This property ensures the desired piston effect. It is also necessary to ensure the compatibility of the scraping liquid (R) with the compounds (C) which are pulled off the inner wall of the capillary tube by checking that the scraping liquid does not damage these compounds.

C. Identification of the Presence of Compounds Circulating Inside the Analysis Tube Once the compounds have been concentrated at the front (F) of the scraping liquid, a first step involves detecting their presence on the front (F). A universal, non-destructive detection technology may be chosen to maintain the integrity of the compounds (C) contained inside the front and to leave open the possibility of later analyzing these contents in detail. The detector (5) selected should be able to function properly on a capillary tube (1) in which the liquid to be analyzed will circulate. Detection using UV absorption is based on a principle which is well-adapted to this dual requirement. However, it is limited in terms of sensitivity. To compensate for this lack of sensitivity, a device emitting deep UVs (with a wavelength under 300 nm) may be used. With excitation wavelengths of this type, it is possible to induce a so-called native fluorescence signal. Using these lasers in combination with appropriate optical cells provides a significant improvement in terms of sensitivity, particularly with detection by UV absorption while maintaining the universal, non-destructive advantages of this type of detection. (Ref. 224 nm deep-UV laser for native fluorescence, a new opportunity for biomolecules detection, C. Bonin et al., J. Chromatography A. 2006), The optical device (5) used in the example is based on the principle of detection by native fluorescence. Here, the optical device described in French Patent No. 2, 869,686 can be used to advantage, since it is compatible with the use of capillary tubes, as well as with the excitation wavelength of a 224 nm deep-UV laser. The optical device described in this patent is based on the utilization of a hollow reflective elliptical cell.

The capillary tube (1), which includes a previously prepared window (made by removing a few millimeters of the protective layer in such a way as to bare the glass of the capillary tube), is installed at a focal point of the elliptical cell orthogonally to its major axis, with the window focused on this same focal point. The incident laser beam lights the capillary tube (1) at this focal point at an angle of less than 90°. The fluorescence signal emitted by the compounds (C) circulating in the capillary tube is emitted on this focal point and is collected at the second focal point of the elliptical cell.

Another advantage of this device is that it can be placed anywhere along the length of the capillary tube. It can thus be positioned more or less closely to the sampling point, according to the method chosen for air aspiration and for creating the front containing compounds (C) at the front (F) of the scraping liquid (R). It also allows changing the capillary tube without taking special precautions, which can be useful for optimizing measurement yield from the device.

The syringe pump (3) which is used to create a deposit (D) on the inner walls of the capillary tube through adiabatic expansion can also be used to aspire the scraping liquid (R) on the front (F) of the scraping liquid (R) circulating in the capillary tube (1). This will create a sort of plug where the compounds (C) contained in the deposit (D) will be concentrated. The syringe pump (3) and the hermetically sealed bottle (4) can also be used to advantage in the assembly described above.

When the front (F) passes by the detector, the occurrence of a fluorescence signal indicates the presence of compounds (C) at the front (F) of the scraping liquid (R). It is also possible to use an optical device equipped with a monochromator and a light detector to obtain the simultaneous detection of a light spectrum as a diode array, or a CCD camera of the type described in FR 2,869,686, in such a way as to detect the fluorescence emission spectrum of the compounds (C) contained at the front (F) with wavelengths between 280 nm and 2 µm. The shape of this spectrum can provide useful information on the nature of the compounds (C) contained at the front (F).

D. Identification and Quantification of Compounds Collected Using the Analysis Tube The compounds at the front (F) of the scraping liquid (R) may be extremely varied and include particles, microorganisms, molecules, etc. To carry out analysis of them, partial vacuum is maintained inside the capillary tube (1) and the enclosure (4) after the front (F) moves beyond the native fluorescence detector (5). The front of the scraping liquid thus arrives at the end of the capillary tube without major deformation. In this way, the nature of the front is preserved, and its composition does not vary.

Figure 7:
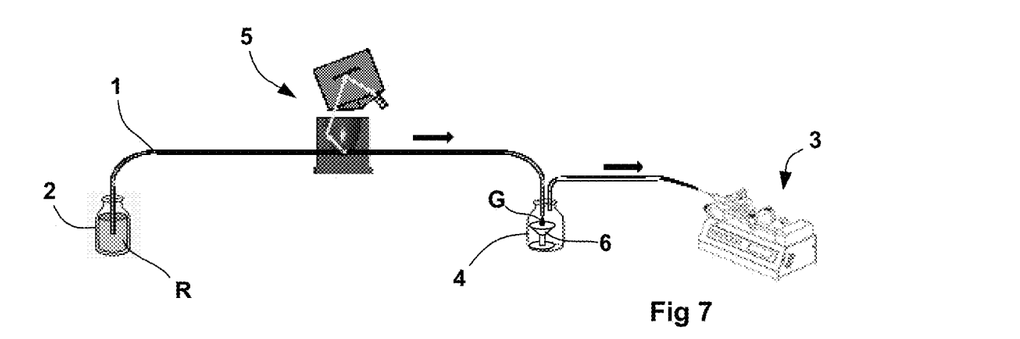

As shown in FIG. 7, by maintaining the vacuum condition in the capillary tube, the first drop (G) formed at the capillary tube outlet in the hermetic reservoir (4) can be collected and analyzed. A container (6) may be placed in the hermetically sealed reservoir (4) to collect the first drop (G) of liquid. This container (6) can be combined with homogenization methods appropriate for conditioning the liquid in the container.

The technologies which enable the essential functions of identifying and quantifying the compounds (C) found at the front are well known. A measuring technique such as capillary electrophoresis, which is appropriate for low sample quantities and relatively easy to automate, may be used. In the present case, this technology is well adapted because the capillary tube (1) and the native fluorescence detector (5) used to detect the presence of compounds can also be used for the electrophoretic separation and quantification of compounds (C) contained inside the front.

It is possible to use this same native fluorescence detector (5) with a deep-UV laser to analyze the signals emitted by the passage of different compounds (C) inside the capillary tube and separated by the action of a potential difference applied between the capillary tube input and output ends. The analysis of signals obtained in terms of amplitude, spectrum and appearance over time enables obtaining identification and quantification indications by comparison with the signal obtained previously from a pure compound.

It is also possible to use identification methods such as high-pressure liquid chromatography, which are, however, more burdensome to implement.

Figure 8:
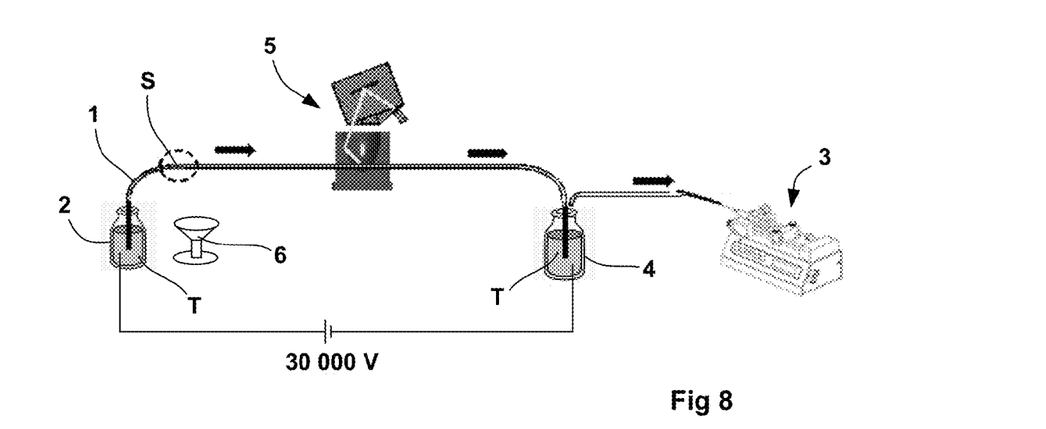

For electrophoretic separation, electrodes are placed at the two ends of the capillary tube, as shown in FIG. 8. One end of the capillary tube can be alternately dipped into the container (6) holding the sample to be analyzed, which is formed by a drop (G) of the scraping liquid front, and then into a bottle containing a buffer liquid (T). This operation can be manual or automatic. The other end of the capillary tube is placed inside the bottle designed to hold the buffer liquid (T) coming from the capillary tube. This bottle can be maintained in under vacuum by the pump (3).

Voltage applied by the generator between the two capillary tube ends ranges from 20,000 V to 30,000 V. The instrument also includes the necessary modules for carrying out electrophoretic separation, such as a high-voltage generator, temperature regulation for the capillary tube and the appropriate acquisition and tracking software.

The following steps may be performed:

Step 1

With reference to FIGS. 3 and 4, the capillary tube (1) is cleaned using the appropriate cleaning liquid (W). The end of the capillary tube is dipped into a bottle (2) which has been filled with this cleaning liquid (W), as illustrated in FIG. 4. The cleaning liquid can be water, a sodium hydroxide solution, an acid-based solution, etc. The cleaning liquid is aspirated by a pump (3) and is recovered from the capillary tube output end in the bottle (4). The native fluorescence detector (5) is used during this cleaning operation to verify that the capillary tube has been properly cleaned. Cleaning time depends on the results obtained using the native fluorescence detector.

As an example, a cleaning procedure may include successive aspirations of air and water. Therefore, it is important to select a perfectly stable reference for the air used. This can be the air (A) contained in a bottle (2) which has previously been checked for the quality of its gaseous content, as illustrated in FIG. 3. It should be noted that this air (A) can be used as a reference for later measurements. Next, the end of the capillary tube is dipped into the cleaning liquid (W), as illustrated in FIG. 4.

Figure 9:
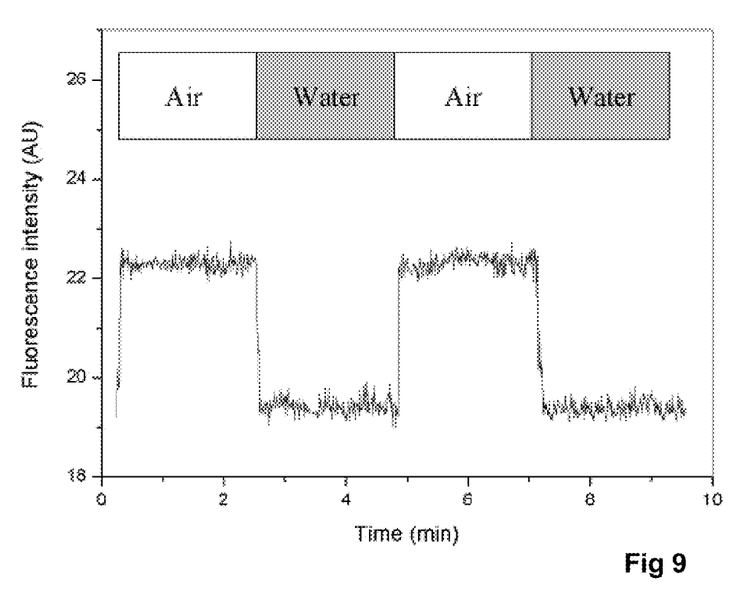
FIG. 9 is a diagram representing the signal emitted successively by the water and the air used to clean the capillary tube.

The cycle can be repeated as often as necessary to verify the stability and repeatability of the cleaning operation. When the capillary tube is clean, the output signal of the native fluorescence detector appears as shown in FIG. 9. This measurement enables noting whether the cleaning liquid (W) contains any polluting elements and confirming cycle repeatability.

Step 2

The first end (E) of the capillary tube is taken out of its bottle to be positioned in such a way as to take a sample of the air to be analyzed, as illustrated in FIG. 5. The pump (3) is turned on for the length of time needed to create enough deposit (D) at the entrance (E) of the capillary tube by creating an adiabatic expansion, as described above.

As an example, for gas vapors and an air flow of 75 µl/min, aspiration time is ten minutes. When the air is being sucked in, the native fluorescence detector is able to detect the compounds (C) contained in the air. Among other factors, the level of detection depends on the elements contained in the air and the conditions under which the air is aspired, the internal diameter of the capillary tube and the aspiration flow rate.

Figure 10:
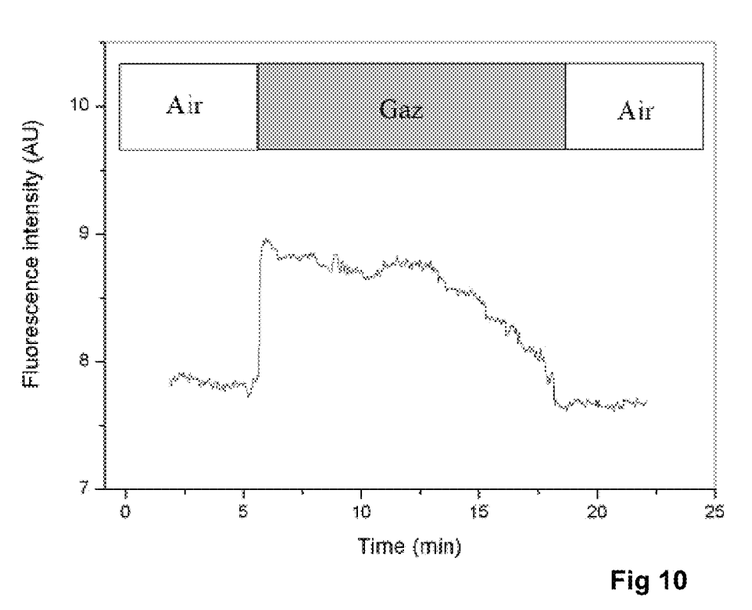
FIG. 10 is a diagram representing the signal emitted by the passage of the reference air, followed by the air to be analyzed (in this case, gasoline vapor)

The output signal of the native fluorescence detector appears as illustrated in FIG. 10. In this particular example, the presence of compounds (C) in the aspirated air is shown, and this presence decreases over time.

The phenomenon of fluorescence signal decay corresponds to the creation of an adiabatic expansion at the entrance to the capillary tube since the depositing of a compound at the capillary tube input causes a reduction in the aspiration diameter. When this diameter narrows, adiabatic expansion increases and the quantity of aspired air decreases. Logically, then, the signal collected by the native fluorescence detector decreases. It should be noted that if the aspiration pump has been turned on for too long, the capillary tube will become clogged.

The presence or absence of compounds is information which can already be used for a first verification. Compounds (C) contained in the deposit (D) are undetected by means used to analyze the air which have been placed upstream from the place where these particles are deposited and that this would tend to distort the nature of the results thus obtained.

Step 3

Figure 6:
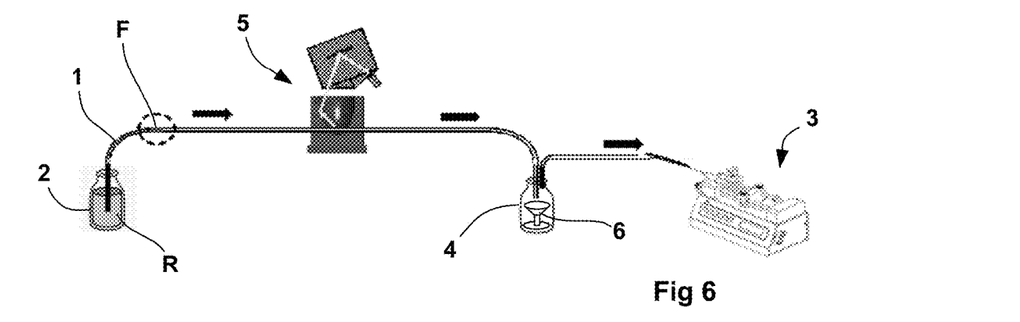

The first end of the capillary tube (1) is dipped into a bottle filled with a scraping liquid (R), as illustrated in FIG. 6. The scraping liquid (R) is sucked up by the vacuum created inside the hermetically sealed bottled (4) by the pump (3), and the front (F) carries the deposit (D) of compounds (C) laid down at the entrance (E) to the capillary tube (1). The front (F) first circulates to the window of the capillary tube placed under the native fluorescence detector (5) to ensure the detection of compounds (C) contained at the front, and then to the other extremity of the capillary tube. Finally, it is collected in the container (6) designed for this purpose, as illustrated in FIG. 7.

Figure 11:
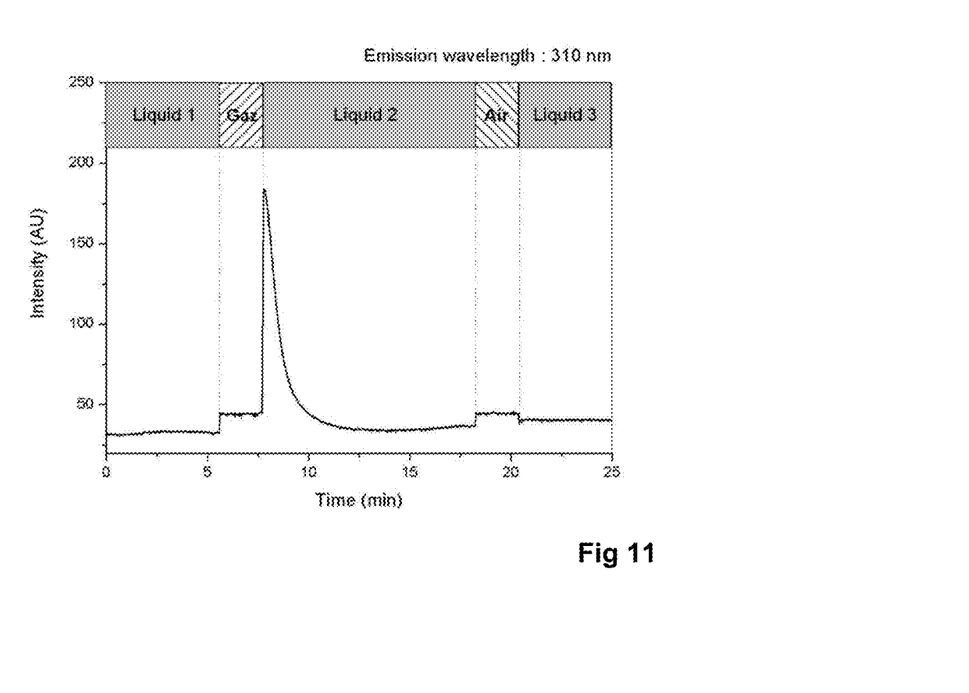
FIG. 11 shows the intensity of fluorescence of a given wavelength emitted by the passage of a front across the native fluorescence detector.

Operating time is calculated in such a way as to ensure that the liquid circulating inside the capillary tube arrives all the way to the end which has been placed in the container (6), where a drop (G) of liquid is collected. The native fluorescence detector (5) is used during this operation to identify the presence of compounds (C) at the front (F) of the scraping liquid (R). The native fluorescence detector output signal for a wavelength of 310 nm appears as illustrated in FIG. 11. The detection peak corresponds to the passage of the front (F) in which the compounds (C) are concentrated.

When the front (F) is identified by the native fluorescence detector (5), it is also possible to carry out a spectral analysis of the signal to obtain qualitative or quantitative information on the compounds (C) contained inside the front (F). This spectral analysis is obtained by replacing the photomultiplier tube with a CCD camera or a diode array, or by using several photomultipliers.

Figure 12:
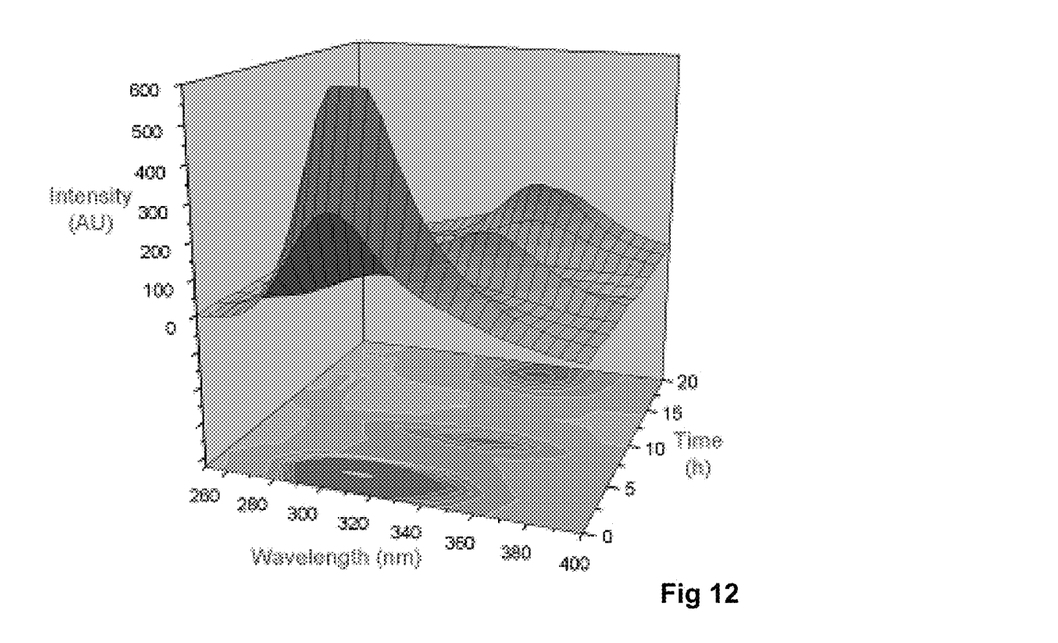
FIG. 12 shows the spectral images formed by the passage at regular intervals of a front across the native fluorescence detector.

Thus, in the case of analyzing compounds emitted by an odifeous liquid, which is most often perceptible by the sense of smell, an evolution of the spectral response over time may be observed. By carrying out a certain number of measurement cycles, a temporal diagram may be created, like the one illustrated in FIG. 12, which represents a sort of smell signature for the odiferous liquid.

Step 4

When collection of the compounds (C) contained inside the front (F) is finished, the capillary tube is cleaned according to the procedure described in Step 1 with reference to FIGS. 3 and 4.

Step 5

The capillary tube (1) is then conditioned for electrophoretic separation. The two ends of the capillary tube are dipped into bottles filled with buffer liquid (T), a general term used to describe the liquid designed to ensure electrophoretic separation. In a first step (see FIG. 8), the capillary tube (1) is filled with buffer liquid by circulating this liquid inside the capillary tube. A pump (3) is used for this filling.

Next, the container (6) holding the front (F) of liquid collected at the previous step and including the compounds (C) to be analyzed is placed at one end of the capillary tube in order to introduce a sample (S) of liquid to be analyzed into the capillary tube, using either vacuum created by the pump or an electric field generated by the high-voltage generator.

When the sample (S) has been injected, the end of the capillary tube is once again dipped into the bottle filled with buffer liquid (T), and separation can begin under the action of an electric field produced by the generator. Voltage applied between the terminals is around 30,000 V.

The passage of compounds (C) under the native fluorescence detector generates peaks which enable identifying individually separated compounds by comparing the time it takes for the signal to appear with the time it takes for the signal from a pure control compound to appear. It is also possible to quantify the compounds by measuring the signal areas of these peaks with reference signals previously obtained by measuring control samples containing a pure compound.

Of course, all five of these steps can easily be automated, in particular when the means used (5) for analyzing with native fluorescence and electrophoresis are identical.

Thus, novel methods and systems have been shown and described. Various changes and substitutions may of course be made without departing from the spirit and scope of the invention. The invention, therefore, should not be limited except by the following claims, and their equivalents.

The invention claimed is:

1. A method for analyzing traces of one or more compounds present in a volume of air, comprising:
    flowing the air through an analysis tube;
    cooling the air at an entrance of the analysis tube to cause condensation and deposition of the compounds on inner walls of the analysis tube;
    flowing a scraping liquid through the analysis tube, said liquid, when entering into the analysis tube, having a front wherein traces of the compounds are preferentially concentrated via the scraping liquid scraping the compounds off of the inner walls of the analysis tube, said scraping liquid selected to not damage the compounds; and
    analyzing the compounds at said front of the liquid, without removing the compounds from the analysis tube.

2. The method of claim 1 wherein the analysis tube is a capillary type tube having an internal diameter of less than 700 µm.

3. The method of claim 1 with the cooling performed via an adiabatic expansion of the air.

4. The method of claim 1 further including cooling the air by cooling an outer wall of the analysis tube using refrigeration.

5. The method of claim 1 wherein the analyzing includes analyzing a spectral response of the front of liquid.

6. The method of claim 5 wherein the analyzing includes use of native fluorescence.

7. The method of claim 1 further including analyzing the air over given time intervals.

8. The method of claim 1 further including collecting the front of the liquid in a container located at an output end of the analysis tube.

9. The method of claim 1 wherein the scraping liquid comprises water, alcohol, sodium hydroxide or hydrochloric acid.

10. The method of claim 1 with the analysis tube comprising a capillary tube and further including collecting traces of compounds in the capillary tube and analyzing the compounds optically without removing the compounds from the capillary tube.

11. The method of claim 10 with the analyzing including using a single detector to perform native fluorescence and capillary electrophoresis.

12. The method of claim 1 further including directing an inlet of the analysis tube alternately toward the volume of air and then toward a bottle containing a scraping liquid and a bottle containing a buffer liquid.

13. The method of claim 1 further including directing an inlet of the analysis tube alternately toward the volume of air and then toward a bottle containing a scraping liquid and a bottle containing previously collected liquid.

14. A system for analyzing traces of compounds present in air, including:
    a fluorescence detector positioned to emit an excitation beam on a flow of matter in a transparent analysis tube, an optical device which targets the excitation beam, and a light detector positioned to collect fluorescence emitted by flow of matter;
    a circulator connected to the analysis tube for creating a liquid fluid and a gaseous fluid pass successively through the analysis tube from an inlet to an outlet of the analysis tube; and
    a cooler adjacent to the inlet of the analysis tube; wherein the optical device comprises:
    an elliptical rotating cavity arranged so that the excitation beam and the analysis tube cross the optical device through passageways inside the optical device;
    wherein an axis of the laser beam and an axis of the analysis tube are focused on focal points of the optical device and are orthogonal to an axis of revolution of the optical device, and form an angle between them of less than 90°; and
    with the point of excitation of the matter circulating inside the analysis tube corresponding to the focal point of the cavity and that light emitted or transmitted by the flow of matter circulating inside the analysis tube through an opening located near the second focal point of the optical chamber can be collected from outside the device.

15. The system of claim 14 with the excitation beam comprising a deep-UV laser.

16. The system of claim 14 with the circulator comprising a vacuum source connected to the outlet of the analysis tube.

17. The system of claim 16 with the vacuum source comprising an aspiration pump.

18. The system of claim 14 wherein the analysis tube comprises a capillary tube with an internal diameter of less than 700 µm.

* * * * *